US010053589B2

(12) United States Patent
Hwang et al.

(10) Patent No.: US 10,053,589 B2
(45) Date of Patent: Aug. 21, 2018

(54) SURFACE TREATMENT COMPOSITON FOR FORMING SELF-ASSEMBLED COATING CAPABLE OF BEING EASILY COATED, REMOVED OR RECOATED

(71) Applicant: POSTECH ACADEMY-INDUSTRY FOUNDATION, Pohang (KR)

(72) Inventors: Dong Soo Hwang, Pohang (KR); Jin Hwa Heo, Gwangju (KR); Dong Yeop Oh, Seoul (KR)

(73) Assignee: POSTECH ACADEMY-INDUSTRY FOUNDATION, Pohang-si (KR)

( * ) Notice: Subject to any disclaimer, the term of this patent is extended or adjusted under 35 U.S.C. 154(b) by 237 days.

(21) Appl. No.: 14/952,989

(22) Filed: Nov. 26, 2015

(65) Prior Publication Data

US 2016/0090489 A1 Mar. 31, 2016

Related U.S. Application Data

(63) Continuation-in-part of application No. PCT/KR2014/002980, filed on Apr. 7, 2014.

(30) Foreign Application Priority Data

May 29, 2013 (KR) .................. 10-2013-0061085

(51) Int. Cl.
  *C09D 7/12* (2006.01)
  *C09D 5/00* (2006.01)
  (Continued)

(52) U.S. Cl.
  CPC ............ *C09D 7/1233* (2013.01); *A61L 29/08* (2013.01); *A61L 31/08* (2013.01); *B05D 5/005* (2013.01);
  (Continued)

(58) Field of Classification Search
  CPC ...................................................... C08G 77/04
  (Continued)

(56) References Cited

U.S. PATENT DOCUMENTS

2011/0105712 A1* 5/2011 Jiang .................. G01N 33/6845
528/26

FOREIGN PATENT DOCUMENTS

CN 102634792 A 8/2012

OTHER PUBLICATIONS

Ye et al., Bioinspired catecholic chemistry for surface modification, 2011, Chemical Society Review, vol. 40, pp. 4244-4258.*

(Continued)

*Primary Examiner* — Dah-Wei D. Yuan
*Assistant Examiner* — Andrew J Bowman
(74) *Attorney, Agent, or Firm* — Lex IP Meister, PLLC (57) ABSTRACT

The present invention relates to a surface treatment composition for forming a self-assembled coating layer which is easily coated and removed and a surface treatment method, where the self-assembled coating layer can be easily formed because of use of a compound having the hydroxyl groups as a diol are attached to an ortho position of a benzene ring and be removed by treatment of $Al^{3+}$ or $Fe^{3+}$. Thus, the surface can be reused by forming a new self-assembled coating layer, thereby making the surface treatment composition be applied to various researches and industrial fields of the self-assembly coating layer which are used for reduction in metal abrasion resistance, introduction of a chemical functional group for detecting a biomolecule, the surface hydrophilicity, introduction of an antifouling property to the surface, and the like.

9 Claims, 9 Drawing Sheets (51) Int. Cl.
  A61L 29/08    (2006.01)
  A61L 31/08    (2006.01)
  B05D 5/00     (2006.01)
  C09D 127/22   (2006.01)
  C09D 171/02   (2006.01)
  C09D 7/63     (2018.01)
  B05D 1/18     (2006.01)

(52) U.S. Cl.
  CPC .............. *C09D 5/002* (2013.01); *C09D 7/63* (2018.01); *C09D 127/22* (2013.01); *C09D 171/02* (2013.01); *B05D 1/185* (2013.01)

(58) Field of Classification Search
  USPC .......................................... 528/26; 427/385.5
  See application file for complete search history.

(56) References Cited

OTHER PUBLICATIONS

Qian Ye, et al., "Bioinspired catecholic chemistry for surface modification", Chem. Soc. Rev., 2011, vol. 40, pp. 4244-4258.

Jeffrey L. Dalsin, et al., "Protein Resistance of Titanium Oxide Surfaces Modified by Biologically Inspired mPEG-DOPA", Langmuir, 2005, vol. 21, pp. 640-646.

Ying Liu, et al., "Amination of surfaces via self-assembly of dopamine", Journal of Colloid and Interface Science, Jun. 14, 2011, vol. 362, pp. 127-134.

* cited by examiner

SURFACE TREATMENT COMPOSITON FOR FORMING SELF-ASSEMBLED COATING CAPABLE OF BEING EASILY COATED, REMOVED OR RECOATED

TECHNICAL FIELD

The present invention relates to a surface treatment composition for forming a self-assembled coating layer which is easily coated, removed or recoated, and particularly, a surface treatment composition for forming a self-assembled coating layer, the composition including a compound in which a hydroxyl group, as a diol, is attached to an ortho position of a benzene ring, and a surface treatment method.

BACKGROUND ART

Self-assembled monolayer (SAM) is a monolayer coated on a specific surface at a molecular level, and the self-assembled coating layer consists of a head group capable of spontaneously forming a strong bonding with a target surface and a head group capable of introducing desired chemical/physical properties onto the coated surface. For recent three decades, many efforts have been made to develop self-assembled coating layers having various functionalities, because self-assembled coating layers have an advantage of easily providing the surface with functionality and thus can be economically applied to various fields. Typically, corrosion of metals can be effectively prevented by coating the metals with the self-assembled coating layer to block direct exposure to external environment. In addition, the self-assembled coating layer controls the coefficient of friction of the surface and thus applied to various fields such as reduction in metal abrasion resistance, introduction of a chemical functional group for detecting a biomolecule, hydrophilicity of the surface, introduction of an antifouling property to the surface, and the like.

However, once contaminated, the self-assembled coating layer may also cause a reduction in the provided functionality or corrosion of surface under the coating. Therefore, studies on the self-assembled coating layer are faced with the challenge of recovering the contaminated surface or maintaining the surface uncontaminated. Many methods have been attempted to remove the contaminated self-assembled coating layer, but they have problems. Most of the methods damaged the surface or did not give satisfactory removal results, upon removing the contaminated self-assembled coating layer. Recently, a self-assembled coating layer to be easily removed has been successfully synthesized. However, the method is very complicated, and has a very low efficiency or a limitation in its application.

DETAILED DESCRIPTION

Technical Problem

To solve the problems of reducing provided functionality or causing corrosion of surface under the coating due to contamination of the self-assembled coating layer, the present invention provides a surface treatment composition which includes a compound, in which a hydroxyl group, as a diol, is attached to an ortho position of a benzene ring, thereby forming a self-assembled coating layer, and a surface treatment method, leading to recoating of the contaminated self-assembled coating layer in a simple manner.

However, the technical problem to be solved in the present invention is not limited to the aforementioned technical problem and other non-mentioned technical problems will be clearly understood by those skilled in the art from the following description.

Technical Solution

In order to solve the above problems, an aspect of the present invention provides a surface treatment composition for forming a self-assembled coating layer, the composition including a compound in which a hydroxyl group, as a diol, is attached to an ortho position of a benzene ring.

Another aspect of the present invention provides a surface treatment method including the step of treating a substrate surface with the surface treatment composition including the compound, in which a hydroxyl group, as a diol, is attached to an ortho position of a benzene ring, so as to form the self-assembled coating layer.

Mussels can be found attached to rocks in coastal areas, and they tightly attach themselves to rocks composed of metal oxide even under wet conditions and environmental stress such as waves. Catechol is one of the adhesive components secreted by mussels, and reversibly binds to metal ions with a high stability constant. Catechol shows different affinities for the metal ion, depending on the type of metal ion. If there are metal ions having different affinities, catechol binds to a metal ion showing a relatively high affinity. The present inventors have developed a surface treatment composition for forming a self-assembled coating layer (SAM) which can be easily coated onto and removed from a particular object by mimicking the chemical mechanism of mussels.

Hereinafter, the present invention will be described in detail.

An aspect provides a surface treatment composition for forming a self-assembled coating layer, the composition including a compound in which a hydroxyl group, as a diol, is attached to an ortho position of a benzene ring.

The compound may be any compound having a structure, in which a hydroxyl group, as a diol, is attached to an ortho position of a benzene ring. For example, the compound may be one or more selected from the group consisting of catechol, DOPA (3,4-dihydroxyphenylalanine), dopamine, N-acetyldopamine, NBAD (N-β-alanyldopamine), methyl-catechol, nitro-DOPA, catechin, tannic acid, ferulic acid, nordihydroguaiaretic acid, hydroxydopamine, hydroxypyrone, mimosine, hydroxypyridine, nitro-dopamine, hydroxyDOPA, TOPA (2,4,5-trihydroxyphenylalanine), and polyphenol.

The compound having the structure, in which a hydroxyl group, as a diol, is attached to an ortho position of a benzene ring, may form a crosslinking bond by a coordinate bond of unshared electron pairs of oxygen molecule with surrounding electrophilic molecules. Therefore, when surface treatment is performed using the surface treatment composition including the compound, a self-assembled coating layer may be formed on the surface by the coordinate bond between the surface and the compound.

A functional substance may bind to the end of the compound. The functional substance may be one or more selected from the group consisting of PEO (polyethylene oxide), PTFE (polytetrafluoroethylene), PMMA (polymethyl methacrylate) and PS (polystyrene). For example, PTFE having excellent water resistance may bind to the end of one or more compounds selected from the group consisting of catechol, DOPA, dopamine, N-acetyldopamine, NBAD, methyl-catechol, nitro-DOPA, catechin, tannic acid, ferulic acid, nordihydroguaiaretic acid, hydroxydopamine, hydroxypyrone, mimosine, hydroxypyridine, nitro-dopamine, hydroxyDOPA, TOPA, and polyphenol.

The surface may be a surface of a metal or metal oxide. for example, the metal may be one or more selected from the group consisting of titanium (Ti), aluminum (Al), iron (Fe), silicon (Si), copper (Cu), tin (Sn), lead (Pb), gold (Au), and zinc (Zn), and the metal oxide may be one or more selected from the group consisting of silicon dioxide, titanium dioxide (titanium dioxide(IV), titanium dioxide(II), titanium dioxide(III), titanium peroxide), aluminium oxide, iron oxide (iron oxide(II), iron oxide(III), triiron tetraoxide), copper oxide (copper oxide(I), copper oxide(II)), tin oxide (tin oxide(II), tin oxide(IV)), zinc oxide, and lead oxide (lead oxide (I), lead oxide (II), lead sesquioxide, lead oxide (IV), lead tetraoxide).

The self-assembled coating layer may be removed from the surface by treatment of $Al^{3+}$ or $Fe^{3+}$. For example, since catechol selectively binds to a metal ion with the highest stability among many metal ions, this property may be used to easily remove the self-assembled coating layer from the surface. $Al^{3+}$ or $Fe^{3+}$ and catechol have very high stability constants, and therefore, the self-assembled coating layer may be removed from the surface by treatment of $Al^{3+}$ or $Fe^{3+}$.

The self-assembled coating layer formed by surface treatment of a substrate with the surface treatment composition may be removed from the surface by treatment of $Al^{3+}$ or $Fe^{3+}$, and the self-assembled coating layer may be formed again by surface treatment of the substrate with the surface treatment composition. Therefore, when the self-assembled coating layer formed on the surface is contaminated, the self-assembled coating layer may be removed, and then it may be reformed by treatment of the surface treatment composition, thereby maintaining the uncontaminated self-assembled coating layer.

The self-assembled coating layer may be a single layer or a multilayer composed of one, or two or more of the single layer.

The thickness of the self-assembled coating layer may be properly adjusted according to the purpose of use of the self-assembled coating layer. For example, the self-assembled coating layer may have a thickness of 10 to 100 nm.

Another aspect provides a surface treatment method including the step of treating a substrate surface with the surface treatment composition including the compound, in which a hydroxyl group, as a diol, is attached to an ortho position of a benzene ring, so as to form the self-assembled coating layer.

The surface treatment method may further include the step of binding the functional substance to the compound, in which a hydroxyl group, as a diol, is attached to an ortho position of a benzene ring, before formation of the self-assembled coating layer. The functional substance may be the same as described above.

The step of binding the functional substance to the compound may include the steps of introducing a protecting group into the compound, binding the functional substance to the end of the protected compound, and removing the protecting group. The compound, in which a hydroxyl group, as a diol, is attached to an ortho position of a benzene ring, for example, catechol is converted into DOPAquinone to lose its reactivity under environment susceptible to oxidation, for example, under neutral and basic environment. To prevent oxidation of the compound until the coordinate bond between the compound and the surface is formed, the step of binding the functional substance may be performed by introducing a protecting group such as triethylsilane, which protects catechol activity and is easily removed by an acid, into the compound.

The surface coating recyclability would be useful for in vitro biomedical applications. For examples, healthcare deviceassociated infection (HDAIs) is one of the most adverse events in high-technology healthcare device such as endoscope, robot-assisted surgery machine, ultrasonic imaging, and dialysis facility due to the nonspecific fouling (contamination) on the surface of the healthcare device. Therefore, proper and frequent cleaning and sterilization of the healthcare facilities are extremely important to prevent the extrinsic infections. However, most biomolecules have a tendency to adsorb nonspecifically onto surfaces/interfaces of the expensive healthcare facilities including endoscopes, surgical robot, and dialysis, and it is difficult to remove completely the contaminated molecules from the expensive healthcare facility after a one-time application to one patient.

According to the coating layer on these devices can be readily removed after use, and then the catechol-based coating can be newly regenerated on the surface of the devices prior to use. The recyclability and price competitiveness of the coating based on the silyl protected catechol chemistry here would be an ideal approach to coat the metal oxide surface of the expensive healthcare device and biochip.

The surface may be a surface of a metal or metal oxide, and specific examples thereof are the same as described above. The self-assembled coating layer can be reversibility coated and removed on the surface and thus be useful for the medical devices such as endoscope, metical staple, inserted part of robot-assisted surgery device, a contacting part of blood dialysis facility, medical catheter. For examples, the medical devices can be recycled by removing and recoating their surface after being used, and can prevent the infection associated with the healthcare device or medical devices.

The surface treatment method may include the step of removing the self-assembled coating layer by treatment of $Al^{3+}$ or $Fe^{3+}$, after formation of the self-assembled coating layer. In the step of removing the self-assembled coating layer, $Al^{3+}$ or $Fe^{3+}$ has very high stability constant with the compound, and therefore, the self-assembled coating layer may be removed from the surface by treatment of $Al^{3+}$ or $Fe^{3+}$ that is, it may be removed by breaking the coordinate bond between the surface and the compound.

The surface and the compound are the same as described above.

The surface treatment method may include the steps of removing the self-assembled coating layer by treatment of $Al^{3+}$ or $Fe^{3+}$, after the step of forming the self-assembled coating layer, and then treating the substrate surface with the surface treatment composition to reform the self-assembled coating layer. These steps are included in the surface treatment method to solve the conventional problem of a reduction in the provided functionality or corrosion of the surface under coating due to contamination of the self-assembled coating layer.

The surface treatment composition of the present invention includes a compound, in which a hydroxyl group, as a diol, is attached to an ortho position of a benzene ring, and therefore, a self-assembled coating layer may be easily formed on the surface and the self-assembled coating layer may be easily removed from the surface by treatment of $Al^{3+}$ or $Fe^{3+}$. Accordingly, there is an advantage of re-formation and recovery of the contaminated self-assembled coating layer. Owing to this advantage, the present invention may be widely applied to research and industrial fields of self-assembled coating layers, such as reduction in abrasion resistance, introduction of a chemical functional group for detecting a biomolecule, hydrophilicity of the surface, introduction of an antifouling property to the surface, and the like.

Hereinafter, the present invention will be described in more detail with reference to the following Examples. However, these Examples are for illustrative purposes only, and the invention is not intended to be limited by these Examples.

Example 1. Coating of Metal Oxide Surface with Self-Assembled Coating Layer 1-1. Preparation of Metal Oxide Silicon wafers were cleaned to remove any contamination using acetone, isopropyl alcohol, and deionized water, serially. Then, titanium (Ti), aluminum (Al), copper (Cu), and gold (Au) were deposited onto the silicon wafer using an e-beam evaporator (Temescal ves-2550, System Control Technology, Livermore Calif.) at a rate of 1 Å/sec to a thickness of 500 Å. Before deposition of the metal layer, the titanium layer was first deposited in a thickness of 100 Å, because it functions to increase adhesion between silicon and other metals. To form a metal oxide layer, the wafers deposited with titanium and aluminum were subjected to $O_2$ plasma treatment (for 5 minutes at 200 W and 300 mT). Further, $Fe_2O_3$ layer was prepared using a sputtering system (ATC2000F, AJAinternational, INC., NorthScituate, Mass.) to a thickness of 100 Å.

1-2. Synthesis of SPC (Triethylsilane Protected Catechol)

Figure 1:
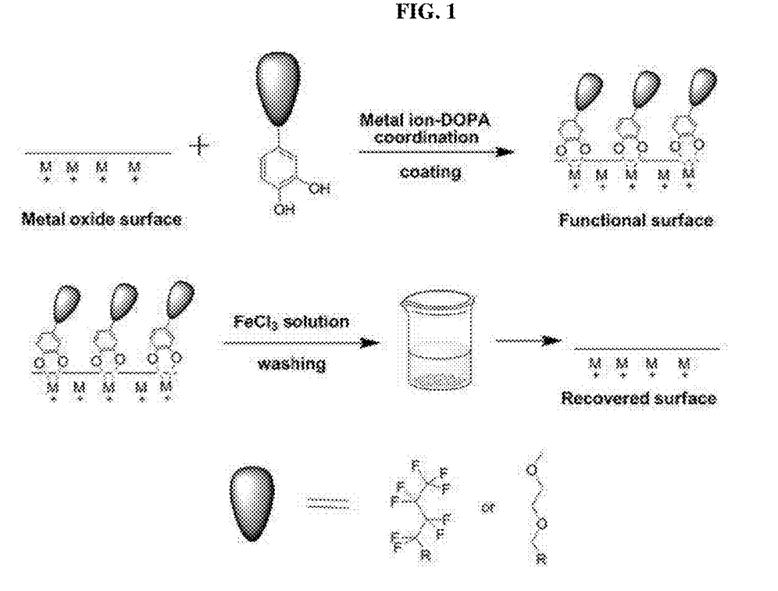
FIG. 1 is a schematic illustration showing processes of coating a self-assembled coating layer on a metal oxide surface and removing the self-assembled coating layer therefrom using functional substance-conjugated catechol.
Figure 2:
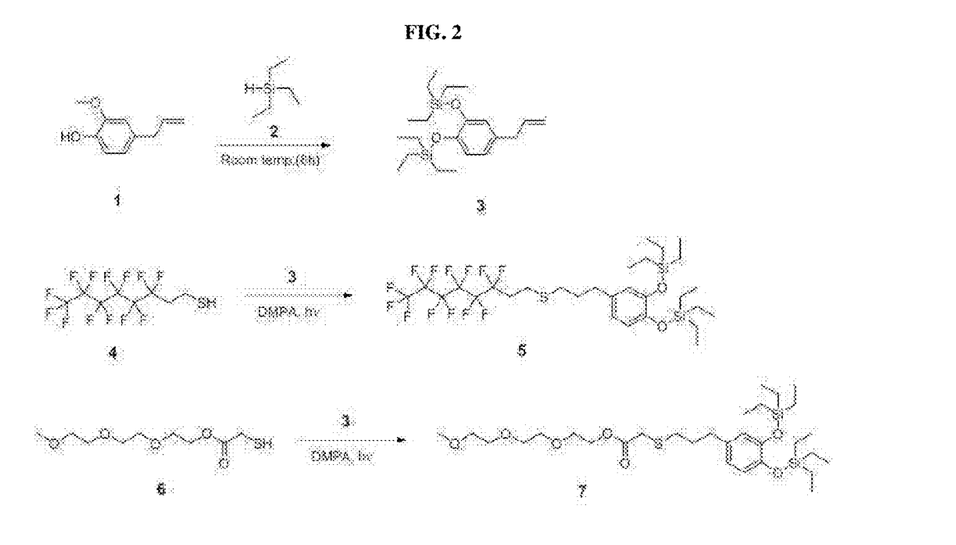
FIG. 2 is a schematic illustration showing synthesis of catechol which is conjugated with a functional substance and is protected with triethylsilane.
Figure 3A:
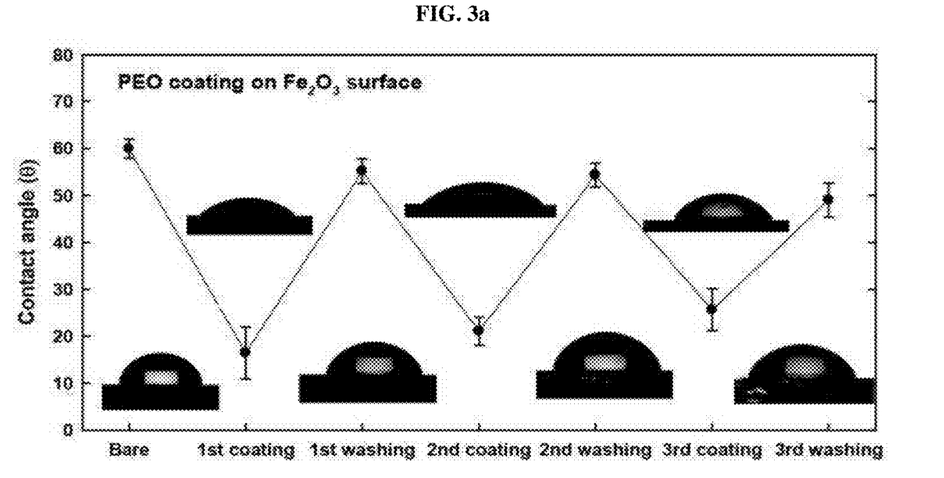
FIGS. 3a to 3d show contact angles of metal oxide surfaces (each $Fe_2O_3$ (FIG. 3a), $Al_2O_3$ (FIG. 3b), $TiO_2$ (FIG. 3c), $SiO_2$ (FIG. 3d)) before coating, metal oxide surfaces on which a self-assembled coating layer is coated according to Example 1.4, and metal oxide surfaces from which the self-assembled coating layer is removed according to Example 2.1.
Figure 3B:
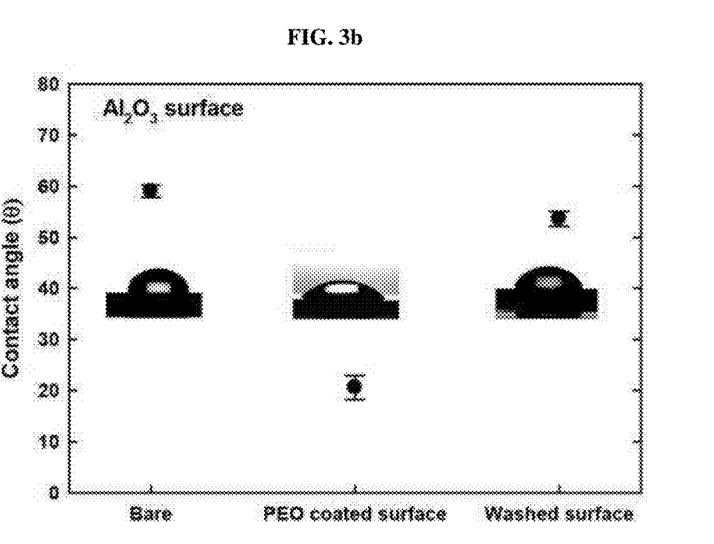
Figure 3C:
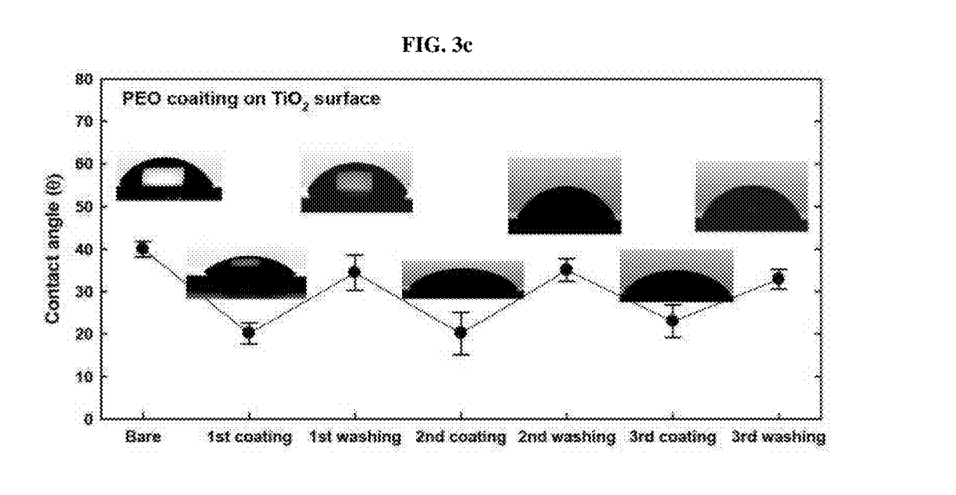
Figure 3D:
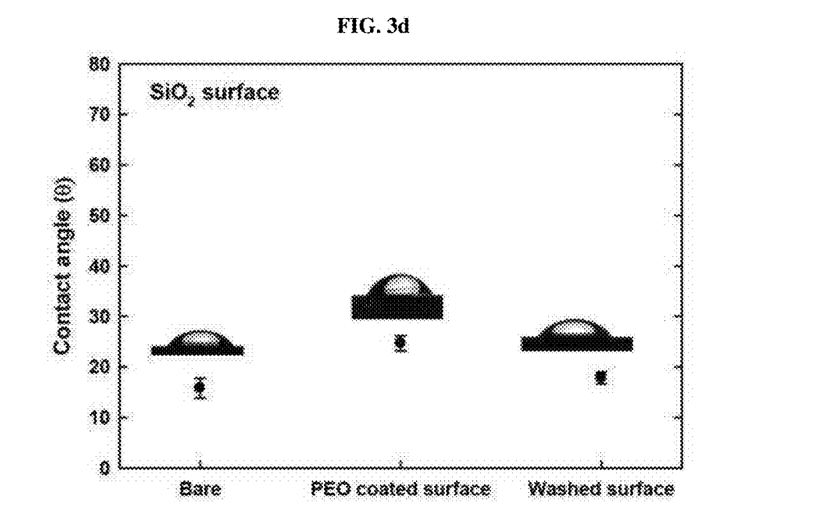
Figure 4A:
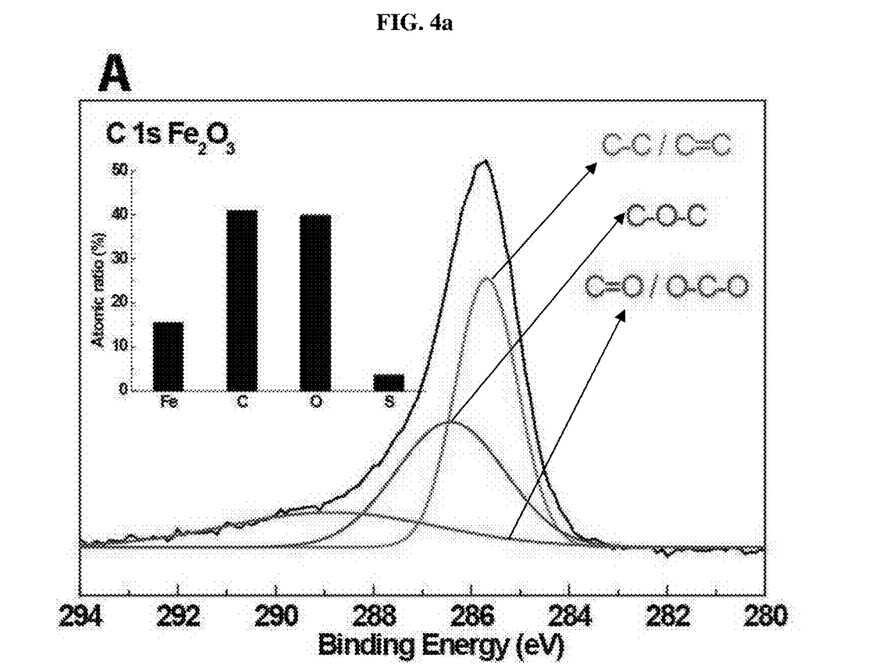
FIGS. 4a to 4d are C1 XPS spectra indirectly showing binding of catechol to the metal oxide surface according to Example 4.
Figure 4B:
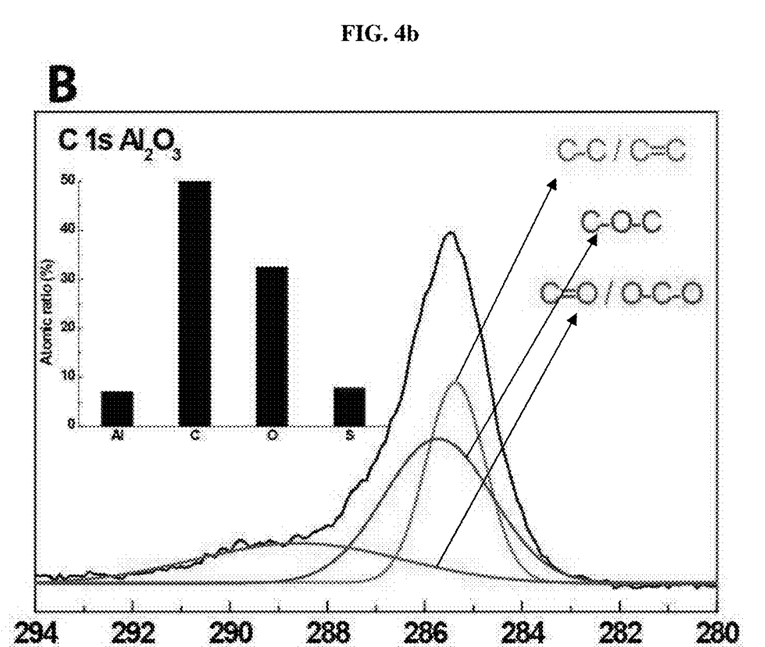
Figure 4C:
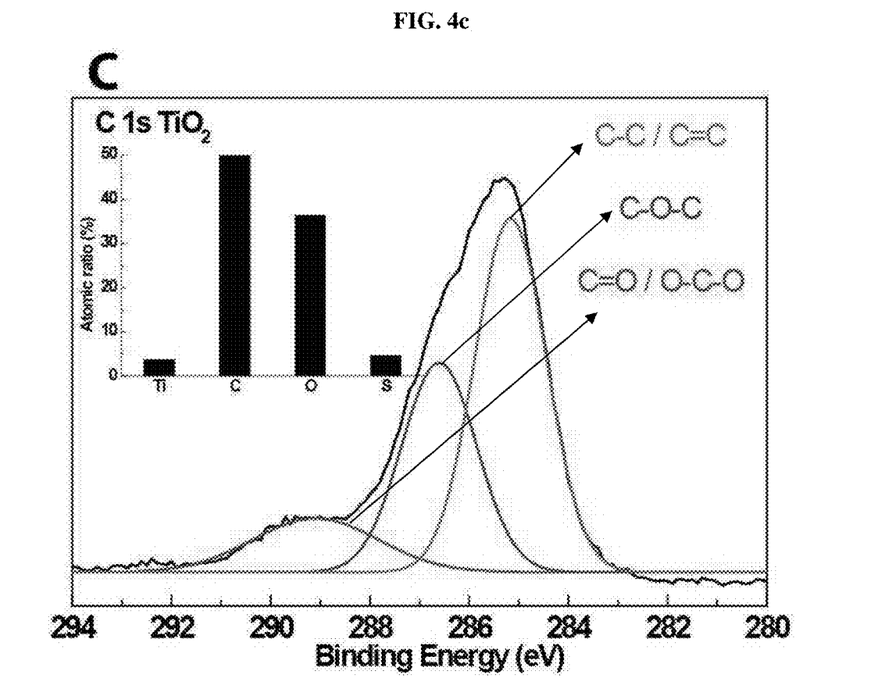
Figure 4D:
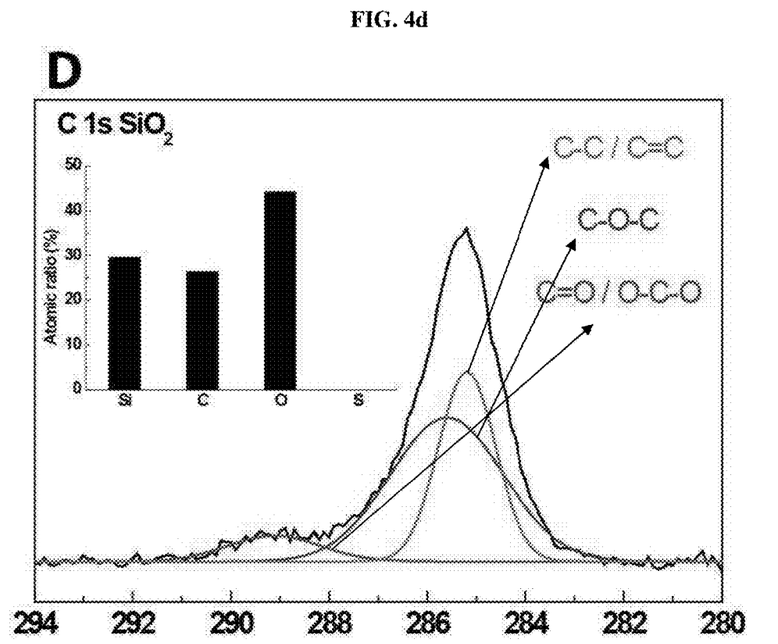

Catechol is converted into DOPAquinone to lose its reactivity under environment susceptible to oxidation, namely, under neutral and basic environment. To prevent oxidation of catechol until the coordinate bond between catechol and the metal oxide surface was formed, SPC (triethylsilane protected catechol) was synthesized. In the experiment, eugenol which can be industrially mass-produced was used instead of expensive catechols, DOPA and dopamine. As shown in FIG. 2, eugenol were first protected by reacting its two oxygen atoms with triethylsilane, thereby synthesizing triethylsilane-protected eugenol having the same structure to SPC (triethylsilane protected catechol).

Reaction of eugenol (1 of FIG. 2) and triethylsilane (2.2 eq. to eugenol) (2 of FIG. 2) was allowed at room temperature for 6 hours using tris(pentafluorophenyl)borane (0.002 eq. to eugenol) as a catalyst. To remove unreacted tris (pentafluorophenyl)borane and dichloromethane, the reacted mixture was passed through a syringe filled with neutral alumina to obtain yellow triethylsilane-protected-eugenol (3 of FIG. 2) (yield: 97-99%).

1-3. Synthesis of Functionalized SPC (Triethylsilane Protected Catechol)

To introduce a functional group such as PEO or PTFE into SPC synthesized in Example 1.2, thiol-terminated PTFE or PEO (polyethylene oxide) was coupled to SPC via 'click' reaction of thiol-end to prepare PTFE (Polytetrafluoroethylene)-conjugated SPC (Example 1-3-3) or PEO-conjugated SPC (Example 1-3-2), as shown in FIG. 2.

1-3-1. Synthesis of PTFE-Conjugated SPC

Triethylsilane-protected-eugenol (1.0 g, 2.64 mmol, 1.0 equiv) (3 of FIG. 2) synthesized in Example 1.2, 3,3,4,4,5, 5,6,6,7,7,8,8,8-tridecafluorooctane-1-thiol (3.01 g, 7.92 mmol, 3.0 equiv) (4 of FIG. 2), and 2,2-dimethoxy-2-phenylacetophenone (33.8 mg, 0.13 mmol, 0.05 equiv) were prepared and put in a 25 ml round-bottom flask containing a magnetic stir bar. 5 ml of dichloromethane as a solvent was added thereto. Impurities were removed from the reaction mixture using dry argon at room temperature for 30 minutes, and placed in a UV-lamp at room temperature for 30 minutes, and purified by column chromatography using a mixture of ethyl acetate and hexane to finally give PTFE-conjugated SPC, ((4-(3-((3,3,4,4,5,5,6,6,7,7,8,8,8-tridecafluorooctyl)thio)propyl)-1,2-phenylene)bis(oxy))bis(triethylsilane) (5 of FIG. 2) (yield: 87%):

$^1H$ NMR (600 MHz, $CDCl_3$): δ=6.73 (d, 1H), 6.62 (m, 2H), 2.72 (m, 2H), 2.60 (t, 2H), 2.53 (t, 2H), 2.36 (m, 2H), 1.87 (m, 2H), 0.99 (t, 18H), 0.76 (q, 12H) ppm.

$^{13}C$ NMR (600 MHz, $CDCl_3$): δ=146.74, 146.17, 134.32, 121.34, 120.98, 120.47, 34.02, 32.29, 31.57, 30.99, 22.71, 6.80, 5.30, 5.25 ppm.

$^{19}F$ NMR (600 MHz, $CDCl_3$): δ=−80.88, −114.42, −121.94, −122.91, −123.45, −126.16 ppm.

Calcd: $[M]^+$ ($C_{29}H_{43}F_{13}O_2SSi_2$) m/z=758.23; found FI-MS: [M+]m/z=758.23.

1-3-2. Synthesis of PEO-Conjugated SPC

First, thiol-terminated PEO was synthesized. 8.2 g of triethylene glycol monomethyl ether (50 mmol), 4.6 g of thioglycolic acid (50 mmol), and 2.15 g of p-toluenesulfonic acid (12.5 mmol) were put in 300 ml of anhydrous toluene, and 5 g of anhydrous magnesium sulfate was added thereto. The reaction mixture was left to reflux in the flask for 12 hrs, and then the reaction mixture was washed with water, brine solution, and $NaHCO_3$. Thereafter, the mixture was purified by column chromatography using a mixture of ethyl acetate and hexane to finally give thiol-terminated PEO, 2-(2-(2-methoxyethoxy)ethoxy)ethyl 2-mercaptoacetate (6 of FIG. 2) (yield: 70%):

$^1H$ NMR (500 MHz, $CDCl_3$): δ=4.115 (m, 2H), 3.55 (m, 2H), 3.48 (m, 6H), 3.37 (m, 2H), 3.21 (m, 3H), 3.13 (m, 2H), 1.92 (m, 1H, —SH) ppm.

$^{13}C$ NMR (500 MHz, $CDCl_3$): δ=170.63 (C=O), 71.75, 70.35, 68.68, 64.47, 58.76, 26.19 ppm.

IR(neat): 2876, 2560, 1733, 1453, 1416, 1352, 1279, 1100, 1038, 961, 850, 700c $m^{-1}$.

Calcd: $[M]^+$ ($C_9H_{18}O_5S$) m/z=238.09; found ESIMS: $[M]+Na^+$ m/z=261.07, $[2M+Na^+]$m/z=49 9.16.

Triethylsilane-protected-eugenol (1 of FIG. 2) (1.0 g, 2.64 mmol, 1.0 equiv), 2-(2-(2-methoxyethoxy)ethoxy)ethyl 2-mercaptoacetate (6 of FIG. 2) (1.9 g, 7.92 mmol, 3.0 equiv), and 2,2-dimethoxy-2-phenyl acetophenone (33.8 mg, 0.13 mmol, 0.05 equiv)) were put in a 25 ml round-bottom flask containing a magnetic stir bar, and 5 ml of dichloromethane as a solvent was added thereto. Impurities were removed from the reaction mixture using dry argon at room temperature for 30 minutes, and placed in a UV-lamp at room temperature for 30 minutes, and purified by column chromatography using a mixture of ethyl acetate and hexane to finally give PEO-conjugated SPC, 2-(2-(2-methoxy-ethoxy)ethoxy)ethyl 2-((3-(3,4-bis((triethylsilyl)oxy)phenyl)propyl)thio)acetate (7 of FIG. 2) (yield: 90%):

$^1$H NMR (600 MHz, CDCl$_3$): δ=6.69 (d, 1H), 6.59 (m, 2H), 4.26 (m, 2H), 3.69 (m, 2H), 3.63 (m, 6H), 3.52 (m, 2H), 3.35 (s, 3H), 3.22 (s, 2H), 2.61 (t, 2H), 2.57 (t, 2H), 1.85 (m, 2H), 0.96 (t, 18H), 0.72 (q, 12H) ppm.

$^{13}$C NMR (600 MHz, CDCl$_3$): δ=170.54, 146.57, 134.43, 121.27, 120.85, 120.31, 72.01, 70.69, 70.68, 70.66, 69.05, 64.4, 59.08, 33.92, 33.55, 32.03, 30.58, 6.76, 6.75, 5.21, 5.16 ppm.

Calcd: [M]$^+$ (C$_{30}$H$_{56}$O$_7$SSi$_2$) m/z=616.33; found ESI-MS: [M+Na$^+$]m/z=639.33.

1.4. Coating of Self-Assembled Coating Layer

PEO-conjugated SPC of Example 1-3-2 was dissolved in a solvent containing acetone and methanol at a ratio of 9:1 to be 2 mg/ml concentration, and then a solid acid-catalyst of (Amberlyst 15) was added in the solution until filling 10% of the total volume. After 3 hours, the silane-deprotected catechol-conjugated PEO solution was filtered through a syringe filter (Whatman®) with 0.2 µm pores. SiO$_2$, TiO$_2$, Al$_2$O$_3$, and Fe$_2$O$_3$ wafers were immersed in the filtered solution for 24 hours. After 24 hours, the wafers were washed with acetone several times, and blown dry under a stream of nitrogen to coat the self-assembled coating layer on the metal oxide.

Example 2. Removal of Self-Assembled Coating Layer from Metal Oxide Surface 100 ml of Tris buffer at pH 8.5 was prepared, and bis-tris and FeCl$_3$ powder were dissolved in buffers at different pH at a concentration of 10 mM and 0.5 mM, respectively to prepare Fe(III) buffer. The Fe(III) buffer was sonicated for 1 hr and centrifuged for 10 min at 400 rpm just prior to use. The self-assembled coating layer-coated metal surfaces were immersed in FeCl$_3$ buffer for 10 minutes, washed with distilled water several times, and blown dry under a stream of nitrogen to remove SAM from the metal oxide surface.

Example 3. Contact Angle Measurement

PEO has excellent biocompatibility and antifouling properties of blocking the adsorption of serum proteins, heterogeneous molecules, and cell adhesion. To examine functionality of PEO which was introduced onto a specific surface using the self-assembled coating layer as in Example 1, that is, to examine coating of PEO, contact angle was measured using a surface analyzer (DSA-100, Kruss Co., Germany) In detail, the metal oxide surfaces before coating of Example 1.1 (each Fe$_2$O$_3$, Al$_2$O$_3$, TiO$_2$, SiO$_2$ surface) and metal oxide surfaces coated with the self-assembled coating layer according to Example 1.4 were placed on a test stage, and 3 µL of a water drop was introduced onto the surface of metal oxide through a microsyringe. Contact angles of water drops on three different areas were measured at room temperature, and the results are shown in FIGS. 3a to 3d.

FIGS. 3a to 3d are graphs showing contact angles of metal oxide surfaces before coating (each Fe$_2$O$_3$, Al$_2$O$_3$, TiO$_2$, SiO$_2$ surface), metal oxide surfaces coated with the self-assembled coating layer according to Example 1.4, and metal oxide surfaces from which the self-assembled coating layer is removed according to Example 2.1.

As shown in FIGS. 3a to 3d, Fe$_2$O$_3$, Al$_2$O$_3$, TiO$_2$, and SiO$_2$ surfaces before coating showed contact angles of 58°, ~60°, ~38° and ~15° respectively. In contrast, when the metal oxide surfaces were coated with the self-assembled coating layer containing catechol, all of them showed contact angles of 18~24°, indicating the formation of stable coatings of self-assembled coating layer on metal oxide surfaces. The minor differences in the contact angle between different metal oxide surfaces are likely due to differences in the coating density of PEO, these differences are assumed to be derived from the difference in stability constant between catechol and the metal ions, and the differences in the distance between oxygen atoms in the metal oxides.

Example 4. X-Ray Photoelectron Spectroscopy

To investigate surface chemistry of self-assembled coating layers coated on Fe$_2$O$_3$, Al$_2$O$_3$, TiO$_2$, and SiO$_2$ surfaces, SAM deposited on metal oxide according to Example 1.1 was examined by X-ray photoelectron spectroscopy (XPS). In detail, X-ray photoelectron spectroscopy (XPS) experiments were performed on a PHI 5800 ESCA System, which was operated at $2 \times 10^{-10}$ Torr with a monochromatic Al Kα (1486.6 eV) anode (250 W, 10 kV, 27 mA). All spectra were calibrated by adjusting to the C 1s peak (284.6 eV) used as a standard, and the results are shown in FIGS. 4a to 4d.

FIGS. 4a to 4d are C1 XPS spectra indirectly showing binding of catechol to the metal oxide surface. FIGS. 4a to 4d represent carbon bonds on Fe$_2$O$_3$, Al$_2$O$_3$, TiO$_2$, and SiO$_2$, respectively.

As shown in FIGS. 4a to 4d, the atomic ratios of Fe, C (carbon), O (oxygen), and S (sulfur) on four metal oxide surfaces were obtained using wide scan of X-ray photoelectron spectroscopy, and Fe ratio was found to be much higher than C ratio on SiO$_2$ surface, indicating that density of the self-assembled coating layer on SiO$_2$ surface is relatively low, compared to those of the self-assembled coating layers on the three different metal oxide surfaces, which is likely due to very low stability constant of the catechol to Si(IV).

Further, the atomic ratios of PEO on the four different metal oxide surfaces were obtained based on X-ray photoelectron spectroscopy data, Fe$_2$O$_3$ being C:S:O=18:17.9: 1.54, Al$_2$O$_3$ being C:S:O=18:11.1:2.6, TiO$_2$ being C:S: O=18:11.7:1.45, and SiO$_2$ being C:S:O=18:30.2:0. Therefore, the ideal atomic ratio (C:S:O) of catechol-conjugated PEO was confirmed to be 18:7:1.

Further, the concentration of oxygen among the atoms constituting the self-assembled coating layer was examined. All of the four metal oxides showed considerably high oxygen ratios, compared to the theoretical oxygen ratio of PEO, and they also showed high S ratios, compared to the theoretical ratio, excluding the self-assembled coating layer on SiO$_2$ surface. This result is likely due to unreacted sulfur atoms of PEO on the metal oxide surface.

Further, peaks corresponding to 285.2 eV, 286.5 eV and 288.8 eV were observed by XPS narrow-scan of the C (carbon) 1 s regions of the self-assembled coating layers on the four metal oxide (Fe$_2$O$_3$, Al$_2$O$_3$, TiO$_2$, SiO$_2$) surfaces. These data imply that each peak represents C—C/C═C, C—O—C, and C═O or O—C—O configurations.

Example 5. NEXAFS Analysis

Near Edge X-ray Absorption Fine Structure (NEXAFS) experiments were performed at 2A line at the Pohang Accelerator Laboratory (PAL) in Korea to obtain C K-edge NEXAFS spectra of SAM on four metal oxide surfaces. In detail, the data was collected in the partial electron yield (PEY) mode. The total energy resolution was about 100 meV with a beam size of 0.5 mm×0.1 mm and the probing depth of ~20 Å. Then, the data were normalized to the beam current using a grid located upstream of the beamline. All data were collected at room temperature at a base pressure of 10-10 Torr or lower. The results are shown in FIG. 5.

Figure 5:
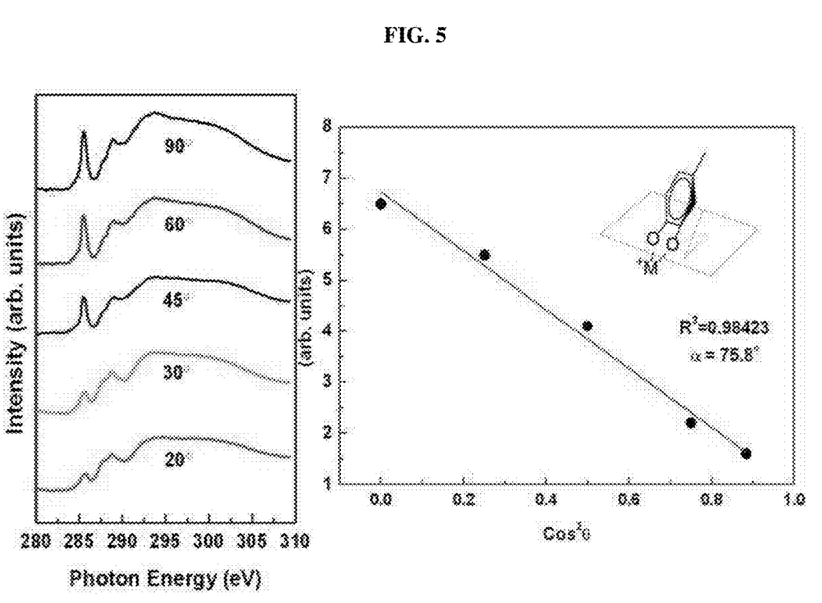
FIG. 5 shows the incident angle of NEXAFS beamline according to Example 5, in which the right graph shows catechol tilted by about 78.8° to the surface.

FIG. 5 shows the incident angle of NEXAFS beamline, in which the right graph shows catechol tilted by about 78.8° to the surface.

As shown in FIG. 5, a single peak was observed at 284.9 eV and multiple peaks were observed in the range of 291 and 303 eV, indicating that the peak at 284.9 eV is ascribable to the $\pi^*$ C=C orbital, and the multiple peaks in the range of 291 and 303 eV are ascribable to $\sigma^*$ orbitals (including C—O at ~295 eV). The C=C and C—O peaks from the X-ray photoelectron spectroscopic studies of Example 4 verified the presence of catechol units and PEO on the metal oxide surfaces, respectively.

To investigate the bonding geometry of catechol groups on the metal oxide surface, data of the average tilted angle ($\alpha$) of catechol groups is needed, and the average tilted angle was examined using the linear function of the $\pi^*$ C=C peak relative intensity vs cos 2θ from the NEXAFS data at more than 2 incidence angles. The result is shown in FIG. 5.

As shown in FIG. 5, the self-assembled coating layer on the $Fe_2O_3$ surface was examined by NEXAFS spectra, and as a result, five different incidence angles were obtained. The catechol rings on the $Fe_2O_3$ surface were found to have a relatively vertical orientation with a tilt angle of ~75.8°. In contrast, SAMs on $TiO_2$ and $Al_2O_3$ surfaces showed incidence angles of 70° and 60°, respectively and were oriented as the "standing up" formation, compared to $\pi^*$ C=C peaks corresponding to the incidence angles of 90° and 30°.

Example 6. AFM (Atomic Force Microscopy) Analysis

In order to examine whether the self-assembled coating layer coating of metal oxide was formed as a single layer or multilayers, atomic force microscopy (AFM) was performed. In detail, the data was collected in the tapping mode of AFM in order to measure roughness of the metal oxide surface before and after coating.

As a result, the root-mean-square (r.m.s) roughness of the self-assembled coating layers on $Fe_2O_3$, $Al_2O_3$, $TiO_2$, $SiO_2$ determined by AFM was 1 nm or less, indicating that the self-assembled coating layer coating of metal oxide was formed as a single layer.

Example 7. Ellipsometric Analysis

In order to examine whether the self-assembled coating layer coating of metal oxide was formed as a single layer or multilayers, ellipsometry of coating on the $SiO_2$ surface was performed using a spectroscopic ellipsometer system (J. A. Woollam Co., Model M-44, Lincoln, Neb.) to determine thickness of the coated self-assembled coating layer. The data of $SiO_2$ among many metal oxides was used, because $SiO_2$ has the smallest number of layers in the multilayer structure to give a highly reliable value in ellipsometry analysis.

As a result, the thickness was 1.2±0.1 nm, highly suggesting that the surface coating formed by using catechol is a single layer.

Example 8. Removal and Recoating of Self-Assembled Coating Layer

The self-assembled coating layers have been widely applied to a variety of fields, such as introduction of an antifouling property to the surface, hydrophilicity of the surface, introduction of a chemical functional group for detecting a biomolecule, reduction in abrasion resistance of metal by controlling the coefficient of friction, or the like. If the self-assembled coating layer is contaminated by external factors, its efficiency is deteriorated. Therefore, removal of the contaminated self-assembled coating layer and recovery of new self-assembled coating layer on the metal oxide surface were tested. Attachment of the self-assembled coating layer on the metal oxide surface in the same manner as in Example 1 and detachment of the self-assembled coating layer from the metal oxide surface in the same manner as in Example 2 were examined by a cycling contact angle test, and the results are shown in FIGS. 3a to 3d.

As shown in FIGS. 3a to 3d, when the $1^{st}$ generation self-assembled coating layer on the metal oxide surface was removed by washing with Fe(III) buffer, contact angles for the metal oxide surface after washing returned to the initial values before coating of the self-assembled coating layer, because Fe(III) has a very high stability constant for catechol, indicating that Fe(III) detached the catechol-conjugated PEO from the metal oxide surface.

Repetitive recovery and removal of the self-assembled coating layers on the $Fe_2O_3$ and $TiO_2$ surfaces were performed in the same manners as in Example 1 and 2, and examined by a cycling contact angle test. The results are shown in FIGS. 3a to 3d.

As shown in FIGS. 3a to 3d, the $Fe_2O_3$ and $TiO_2$ surfaces coated with the $2^{nd}$ generation self-assembled coating layers showed contact angles of 25° or less and 23° or less, respectively. After removal of the $2^{nd}$ generation self-assembled coating layers, the $Fe_2O_3$ and $TiO_2$ surfaces showed contact angles of 50° or less and 33° or less, respectively.

The attachment and detachment efficiency of self-assembled coating layer gradually decreased with the repetitive recovery and removal of the self-assembled coating layer, which may be associated with impurities remaining on the metal oxide surface. It was necessary to wash the coated metals by sonication, but was excluded because it could damage the metal oxide layer, which may influence the experimental results. It is expected that efficiency of SAM may be improved by sonication.

Although an exemplary embodiment of the present invention has been described for illustrative purposes, those skilled in the art will appreciate that the present invention may be implemented in a different specific form without changing the technical spirit or essential characteristics thereof. Therefore, it should be understood that the above embodiment is not limitative, but illustrative in all aspects.

What is claimed is:

1. A method of treating a surface, comprising forming a self-assembled coating layer on a surface by treating the surface with a surface treatment composition comprising one or more compound selected from the group consisting of catechol, DOPA (3,4-dihydroxyphenylalanine), dopamine, N-acetyldopamine, NBAD (N-β-alanyldopamine), methylcatechol, nitro-DOPA, catechin, tannic acid, ferulic acid, nordihydroguaiaretic acid, hydroxydopamine, hydroxypyrone, mimosine, hydroxypyridine, nitro-dopamine, hydroxyDOPA, TOPA (2,4,5-trihydroxyphenylalanine), and polyphenol, wherein the method further comprises removing the self-assembled coating layer by treating with $Al^{3+}$ or $Fe^3$.

2. The method according to claim 1, wherein the compound is connected to a functional substance.

3. The method according to claim 1, wherein the functional substance is connected by introducing a protecting group to the compound, connecting the functional substance to an end of the compound having the protecting group, and removing the protecting group.

4. The method according to claim 2 or claim 3, wherein the functional compound is one or more selected from the group consisting of PEO (polyethylene oxide), PTFE (polytetrafluoroethylene), PMMA (polymethyl methacrylate) and PS (polystyrene).

5. The method according to claim 1, wherein the surface is a surface of the medical device.

6. The method according to claim 1, wherein the medical device is endoscope, metical staple, inserted part of robot-assisted surgery device, a contacting part of blood dialysis facility, or medical catheter.

7. The method according to claim 1, wherein the surface is a surface of a metal or metal oxide.

8. The method according to claim 1, wherein the surface is a surface of one or more metal selected from the group consisting of titanium (Ti), aluminum (Al), iron (Fe), silicon (Si), copper (Cu), tin (Sn), lead (Pb), gold (Au), and zinc (Zn); or of one or more metal oxide selected from the group consisting of silicon dioxide, titanium dioxide, aluminum oxide, iron oxide, copper oxide, tin oxide, zinc oxide, and lead oxide.

9. The method according to claim 1, wherein the method further comprises removing the self-assembled coating layer by treating with $Al^{3+}$ or $Fe^{3+}$ and then forming a self-assembled coating layer.

* * * * *